(12) United States Patent
Zastrow (10) Patent No.: US 11,273,007 B2
(45) Date of Patent: Mar. 15, 2022

(54) HAND-HELD SURGICAL DEVICE, AND PROTECTION DEVICE

(71) Applicant: Frank Zastrow, Heidelberg (DE)

(72) Inventor: Frank Zastrow, Heidelberg (DE)

(*) Notice: Subject to any disclaimer, the term of this patent is extended or adjusted under 35 U.S.C. 154(b) by 53 days.

(21) Appl. No.: 15/569,763

(22) PCT Filed: May 6, 2016

(86) PCT No.: PCT/DE2016/200216
§ 371 (c)(1),
(2) Date: Oct. 26, 2017

(87) PCT Pub. No.: WO2016/180416
PCT Pub. Date: Nov. 17, 2016

(65) Prior Publication Data
US 2018/0125607 A1 May 10, 2018

(30) Foreign Application Priority Data

May 8, 2015 (DE) .......................... 102015208609.7
May 11, 2015 (DE) .......................... 102015208646.1

(51) Int. Cl.
*A61C 1/16* (2006.01)
*A61C 8/00* (2006.01)
(Continued)

(52) U.S. Cl.
CPC .............. *A61C 1/16* (2013.01); *A61B 10/025* (2013.01); *A61B 17/1633* (2013.01);
(Continued)

(58) Field of Classification Search
CPC ........... A61C 1/16; A61C 1/141; A61C 1/084; A61C 8/0089; A61B 17/1633; A61B 17/1635; A61B 17/1637; A61B 10/025
See application file for complete search history.

(56) References Cited

U.S. PATENT DOCUMENTS 2,429,356 A 10/1947 Hicks
3,384,085 A * 5/1968 Hall ................... A61B 17/1633
606/180

(Continued)

FOREIGN PATENT DOCUMENTS

DE 3202193 A1 8/1983
DE 9416194 U1 1/1995
(Continued)

OTHER PUBLICATIONS

International Search Report for PCT/DE2016/200216 dated Oct. 27, 2016.

*Primary Examiner* — Nicholas D Lucchesi
*Assistant Examiner* — Hao D Mai
(74) *Attorney, Agent, or Firm* — Seed Intellectual Property Law Group LLP (57) ABSTRACT

A hand-held surgical device, particularly for use in oral surgery, includes a rotatable tool, a head of the tool having a hollow-cylindrical design, and an active region, particularly for machining bones, being arranged at a distal edge of the head. A protection device is arranged which partially surrounds the distal edge of the tool and in some sections extends in the axial direction beyond the distal edge such that only a circular arc of the distal edge serves as the active region. The protection device may have a connecting element for detachably securing to the hand-held surgical device.

10 Claims, 13 Drawing Sheets

(51) Int. Cl.
*A61B 17/16* (2006.01)
*A61B 10/02* (2006.01)
*A61C 1/14* (2006.01)
*A61C 1/08* (2006.01)

(52) U.S. Cl.
CPC ...... *A61B 17/1635* (2013.01); *A61B 17/1637* (2013.01); *A61C 1/141* (2013.01); *A61C 8/0089* (2013.01); *A61C 1/084* (2013.01)

(56) References Cited

U.S. PATENT DOCUMENTS

| | | | |
|---|---|---|---|
| 3,937,222 A | 2/1976 | Banko | |
| 4,722,685 A * | 2/1988 | de Estrada | A61D 5/00 433/1 |
| 5,755,718 A * | 5/1998 | Sklar | A61B 17/1604 606/170 |
| 6,210,261 B1 * | 4/2001 | Johnson | B24B 55/052 451/451 |
| 6,214,009 B1 * | 4/2001 | Toriumi | A61B 17/32002 606/80 |
| 6,423,078 B1 * | 7/2002 | Bays | A61B 17/32 606/131 |
| 6,561,887 B2 * | 5/2003 | Lai | B24B 23/02 403/362 |
| 7,238,021 B1 * | 7/2007 | Johnson | A61C 1/16 433/1 |
| 7,585,300 B2 * | 9/2009 | Cha | A61B 17/1633 606/80 |
| 7,785,337 B2 * | 8/2010 | Adams | A61B 17/32002 606/180 |
| 8,109,958 B1 * | 2/2012 | Alleyne | A61B 17/1671 606/170 |
| 8,221,424 B2 * | 7/2012 | Cha | A61B 17/1626 606/80 |
| 8,623,021 B2 * | 1/2014 | Ries | A61B 17/1671 606/79 |
| RE44,883 E * | 5/2014 | Cha | A61B 17/1671 606/80 |
| 2005/0165420 A1 | 7/2005 | Cha | |
| 2006/0217751 A1 | 9/2006 | O'Quinn et al. | |
| 2007/0060936 A1 | 3/2007 | Benavitz et al. | |
| 2008/0249553 A1 * | 10/2008 | Gruber | A61B 17/32002 606/171 |
| 2014/0018834 A1 | 1/2014 | Kather et al. | |

FOREIGN PATENT DOCUMENTS

| | | |
|---|---|---|
| DE | 102007060493 A1 | 6/2009 |
| DE | 102008019790 A1 | 10/2009 |
| DE | 102009013451 A1 | 9/2010 |
| DE | 102011012637 A1 | 8/2012 |
| WO | 2009005458 A1 | 1/2009 |

* cited by examiner

HAND-HELD SURGICAL DEVICE, AND PROTECTION DEVICE

This application is a U.S. National Phase Application pursuant to 35 U.S.C. § 371 of International Application No. PCT/DE2016/200216 filed May 6, 2016, which claims priority to German Patent Application No. 10 2015 208 609.7 filed May 8, 2015 and German Patent Application No. 10 2015 208 646.1 filed May 11, 2015. The entire disclosure contents of this application is herewith incorporated by reference into the present application.

The invention relates to a hand-held surgical device, in particular for use in oral surgery, having a rotating tool, wherein a head of the tool is designed as a hollow cylinder, and wherein an functional region, in particular for machining bones, is disposed at a distal edge of the head. Moreover, the invention relates to a protective device, having a connecting element that can be releasably attached to a hand-held surgical device, in particular for use in oral surgery.

Surgical dentists, oral surgeons and maxillofacial surgeons are often confronted with the problem that, as a result of bone atrophy, accidents, periodontitis or tooth extraction, bone material is lost in the oral cavity.

When dental implants for the use of new teeth are planned, it is thus important that these bone deficits are built up in advance, or simultaneously with the placement of the implant, in order that the dental implant has a new foundation and a stable support in the bone.

Autologous bone of the patient remains the ideal for bone regeneration procedures. This is due to the properties of the bone, because autologous bone unites osteogenic, osteoinductive and osteoconductive properties with one another. This means that the bone has the ability to form its own bone tissue, vessels, and also functions as a control structure for the newly formed bone. Bone replacement material, in contrast to autologous bone, has no biological abilities, and functions only in an osteoconductive manner, e.g. it also functions as a guide rail.

When working with autologous bone, numerous methods are known. With larger bone deficits, edentulous bone areas can fundamentally be used as second intraoral extraction points, or alternatively, the tuber maxillae, the anterior nasal spine, the gums, the region of the maxillary sinus in the upper jaw, or the lower jaw, because these exhibit a more cortical nature, and the bone quality is regarded as very good and stable. There are numerous extraction sites in the lower jaw, e.g. edentulous areas such as the chin or the retromolar space.

The bone extraction can take place thereby with various instruments. The concept of the bone extraction is usually similar thereby.

Either three to four predetermined breaking points are created with a so-called Lindemann mill or a piezo-surgery device, or with a small saw, and the block is subsequently broken out with a chisel or other instrument. A disadvantage therewith is that a certain amount of force must be applied to the jaw. For this reason, some physicians shy away from this operation, as well as for the reason that this hammering or breaking the block of bone out of the respective region is also unpleasant for the patient.

Due to their profession, dentists are familiar with rotating instruments and drills. As such, the so-called trephine mill has become established in the field, which is attached to a handle, and has a head in the form of a hollow cylinder. Teeth for machining bones are formed on the distal edge of the head. Trephine mills are used, for example, for preparing implant beds, and have a diameter of ca. 3 mm to 4 mm. Extremely small and narrow cylinders are extracted with these mills, which are only suitable for bone regeneration to a certain extent.

With the devices listed above, ca. three to four cuts or predetermined breaking points must be formed for bone extraction, in order to obtain the required piece of bone. This involves a strong load applied to the patient, and requires a great deal of skill on the part of the surgeon. In particular, care must be taken to avoid injuring the surrounding soft tissue, e.g. cheek or lip tissue, with the surgical tool.

The present invention therefore addresses the object of designing and developing a hand-held surgical device of the type specified in the introduction, such that a reliable bone extraction that is gentle on the patient can be obtained with structurally simple means.

In accordance with the invention, the hand-held surgical device in question is distinguished in that a protective device is disposed thereon, which partially encompasses the distal edge of the tool, and extends in part over the distal edge in the axial direction, such that only a circular arc of the distal edge serves as the functional region.

In a manner according to the invention, it was first realized that, counter to a prejudice on the part of experts in the field, a tool having a head in the form of a hollow cylinder that has a functional region for machining bones is not only suitable for extraction of small drilled cylinders. Instead, such a tool can be used to "peel off" the necessary bone pieces or bone segments from the bone. It has also been realized, in a manner according to the invention, that by placing a protective device thereon, which partially encompasses the head of the tool, in particular in the radial or circumferential direction, and extends in part over the distal edge, just a circular arc of the distal edge of the head can be brought in contact with the bone, thus serving as an effective functional region. As a result of this structural measure, it is possible for a surgeon to peel a basically half-moon shaped piece of bone from the bone, which can be used for bone regeneration. In contrast to the instruments, or tools, known from the prior art, it is not necessary to make three to four cuts or predetermined breaking points. Instead, there is only one predetermined breaking point, and it is not necessary to hammer the bone out. The resulting block can thus then be removed or dislocated without excessive force, which is more gentle on the patient and more pleasant in comparison with known devices and techniques. Consequently, the load imposed on the patient by the operation is minimal. Moreover, the surrounding tissue is protected against injury in an ideal manner by the protective device. Thus, the handling of the hand-held surgical device is particularly simple.

The protective device advantageously encompasses the head such that a circle segment formed by the circular arc has a segment height of 2.5 mm to 3.5 mm, in particular 2.7 mm to 3.3 mm, preferably 2.9 mm. Concretely, the segment height can be adjusted via an adjusting screw, wherein the protective device can be displaced radially in relation to the tool via the adjusting screw. As a result, it is ensured that the tool only penetrates the bone to a certain extent, such that injury to nerves running through the interior of the bone is avoided. Moreover, the dimensions of the protective sheath can be such that the head can only penetrate the bone to a maximum depth of 12 mm to 22 mm, in particular 14 mm to 18 mm, preferably 15 mm in the axial direction, in order to prevent injury to the interior nerves.

In order for the extracted bone piece to be suitable for reconstruction of an implant bearing surface, the dimensions of the protective device can furthermore be such that chords of the circle segment are 8 mm to 15 mm long.

It is of further advantage that the protective device and/or the tool are releasably connected to the hand-held device. The hand-held device can be a conventional angle piece, or handpiece, such as those used by dentists and dental surgeons. The protective device can be attached to the hand-held device via a socket connection, a screw connection, or a bayonet joint. Furthermore, the protective device can be designed such that it rotates in the circumferential direction, so that it can be adjusted to the extraction point of the bone. In concrete terms, the tool can be clamped in the hand-held device. Alternatively or additionally, the tool, in particular its connecting region, or shaft, can be rotatably connected or coupled to the protective device. In addition, a bearing, in particular a roller bearing, a ball bearing race, or a grooved ball bearing race, can be formed between the protective device and the tool. When connecting the connecting region of the tool—e.g. a shaft, normally disposed on such tools—to the hand-held surgical device, the protective device is also connected to the hand-held surgical device. Thus, the connecting region of the tool also serves as a connecting element for the protective device, in order, specifically, to implement a, preferably releasable, connection to the hand-held surgical device.

As has already been explained above, the tool can have a connecting region for connection with a hand-held device, e.g. a dental angle piece or handpiece. Moreover, a rough surface and/or teeth, in particular cutting teeth or saw teeth, can be formed on the distal edge of the head. The rough surface and/or the teeth can form at least a part of the functional region.

In order to prevent a twisting, resulting in slippage, or in order to ensure a "smooth," soft entry of the tool into the bone, a rough surface can be formed on the inner and/or outer wall of the head bordering on the distal edge, which forms a part of the functional region. This allows the surgeon to change directions in the movement of the tool inside the bone.

In an advantageous manner, the rough surface is generated mechanically, through electro-erosion, or by etching. It is also conceivable to create the rough surface through a coating with diamond grit or sapphire grit. Concretely, the tool can be a tool made of metal, e.g. stainless steel, wherein the rough surface is created mechanically, through electro-erosion, or etching, or by a coating of diamond grit or sapphire grit. Due to their hardness, diamond grit in particular offers the possibility of a particularly gentle and quick processing of the bone.

In order to simplify the handling of the tool, markings indicating the penetration depth into the bone can be formed on the outer wall of the head. This provides the surgeon with a simple means for controlling the penetration depth, and thus avoiding injury to the nerves in the bone. It is also conceivable for a penetration barrier to be formed on the head, in order to prevent penetrating too deep into the bone with the tool. This structural measure likewise serves to protect the nerves running through the bone. In particular, the penetration barrier can be implemented as a projection disposed on the inner and/or outer wall of the head. In order to subject the tool and/or the extraction point with a cooling medium—e.g. an NaCl solution—at least one discharge opening can be formed on the tool, wherein the discharge opening has a flow connection to a channel running through the tool.

A particularly gentle processing of the bone is possible when the wall of the head has a thickness of 0.1 mm to 1.5 mm, in particular 0.4 mm to 0.8 mm. A thickness of 0.5 mm has proven to be particularly advantageous, with which the wall of the head exhibits the necessary stability, and a very thin design is obtained, which allows the bone to be treated gently.

It is also conceivable for the distal edge of the head to have a convex, in particular round or oval, cross section. Such a geometry makes it possible for the tool to penetrate the bone in a particularly "soft" manner. Alternatively, the distal edge of the head can have an angular, in particular triangular, cross section, by means of which extremely hard bone layers can be treated in a very gentle manner.

It is also advantageous if the inner diameter of the head is 5 mm to 20 mm, by way of example 5 mm to 10 mm, in particular 5 mm to 8 mm, preferably 5 mm to 6 mm. A head of this size thus offers the possibility of extracting bone pieces of the necessary dimensions from the bones. Alternatively or additionally, the length of the head in the axial direction can be 8 mm to 23 mm, in particular 10 mm to 18 mm, preferably 15 mm. This feature also ensures that the bone piece that is to be extracted is of the necessary size for serving as the foundation for receiving the implant.

The wall of the head can be a continuous, solid form, at least in the region of the rough surface, such that the rough surface forming the functional region is as large as possible. Furthermore, the wall of the head can have holes, at least in the region of the rough surface, or over the entire hollow cylindrical region. The holes can be oval thereby, for example. The holes prevent an overheating of the extraction point or the tool.

In order to create a protective device that is as small as possible, which protects the surrounding soft tissue from the rotating tool, the protective device can be at least partially cylindrical. Ideally, the protective device is cylindrical or partially cylindrical in the region of the hollow cylindrical head.

It is furthermore advantageous if the protective device is composed of two parts, wherein the parts can be joined with an adhesive. In order to prevent recycling, and problems regarding hygiene associated therewith, the adhesive can be selected or adjusted such that it melts during a recycling or cleaning, e.g. autoclaving, such that the protective device can no longer be used. Alternatively or additionally, the protective device can be made of a material that changes its shape and/or color during recycling.

To further improve the handling and to avoid injury to the surrounding tissue, a projection extending radially inward can be formed on the free end of the protective device. As a result, the distal edge of the head is encompassed not only circumferentially by the protective device, but also radially and axially. Thus, a part of the projection can also run radially inside the head.

Furthermore, a preferably round web, running radially over the free end of the protective device can be formed on the free end of the protective device. A depth protection is formed by the web, which prevents the tool form penetrating too deep into the bone. Alternatively, the protective device can be closed at the free end.

In a particularly advantageous manner, at least one discharge opening can be disposed on the protective device, wherein the discharge opening has a flow connection to a channel running through the protective device, in order to supply a cooling medium to the tool, the functional region, and/or the operating point. It is conceivable thereby that the discharge opening has a flow connection to numerous channels and/or that numerous discharge opening are provided. The cooling medium can be a NaCl solution, for example. Moreover, the discharge opening can be configured as a nozzle, such that the cooling medium can be applied over a large surface area, or is discharged in a fine stream.

In order to provide the surgeon with a good view of the operating point, the protective device can have adjacent openings disposed over its circumference. In concrete terms, the openings can be oval. Alternatively or additionally, the protective device can be made of a transparent material, preferably plastic. In order to simplify the handling, it is possible to create depth markings on the outer wall of the protective device.

In an entirely advantageous manner, a guide element, extending axially, can be disposed on the protective device. The guide element makes it easier to insert the device in the "pocket" between the bone and soft tissue. The guide element may be curved at the end away from the handle, in order to ensure a particularly easy insertion into the "pocket."

Also disclosed herein is a protective device which has a connecting element for the releasable connection thereof to a hand-held surgical device, in particular for use in oral surgery, wherein the protective device, when it is connected to the hand-held device, partially encompasses a distal edge of a tool connected to the hand-held surgical device, and extends axially in part over the distal edge, such that only a circular arc of the distal edge serves as the functional region, in particular for machining bones.

The protective device and/or the tool can be designed as described above, and have the features and advantages specified therein with regard to this protective device or this tool. Moreover, the protective device and the tool can have all of the features of the protective device or the tool described in the following description of the figures.

Advantageously, the protective device can be rotatably connected or coupled to the tool, such that the protective device can be supported by the tool, in particular the shaft or connecting region. In particular, the coupling or connection can take place via a bearing, e.g. a roller bearing or ball bearing race or grooved ball bearing race. With such a design, a shaft or connecting region of the tool serves as the connecting element for the protective device, in order to connect the protective device in a releasable manner to a hand-held surgical device. Thus, it is possible to couple the protective device to a hand-held surgical device with structurally simple means.

There are different possibilities for designing and further developing the teachings of the present invention in an advantageous manner. For this, reference is made to the entire disclosure herein, including the following explanations of preferred exemplary embodiments of the invention based on the drawings. Generally preferred designs and developments of the teachings are also explained in conjunction with the explanations of preferred exemplary embodiments of the invention based on the drawings. Therein:

Figure 1:
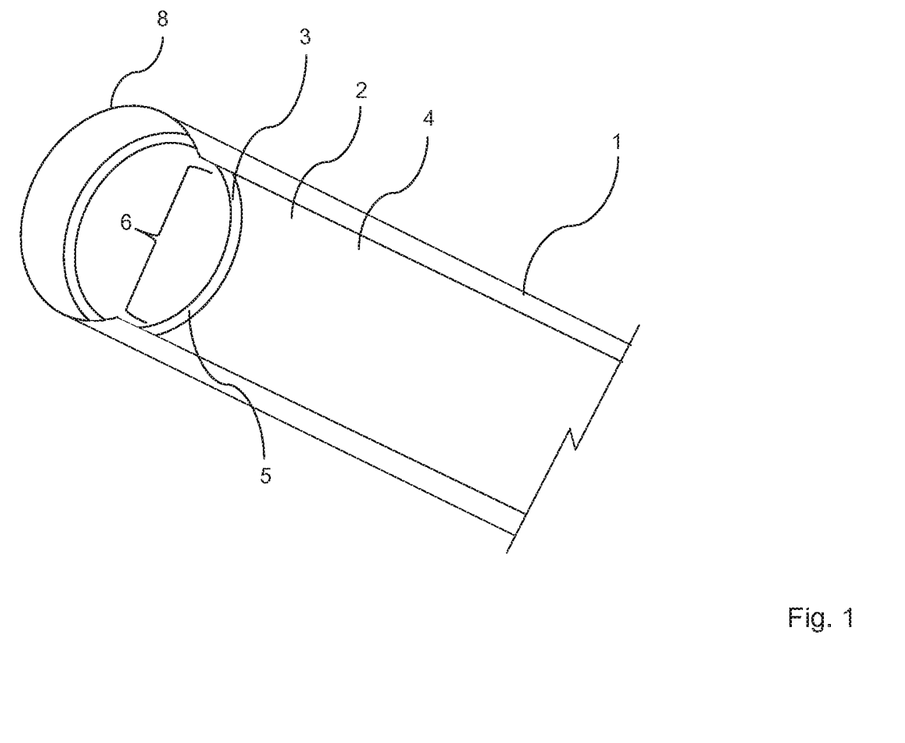
FIG. 1 shows, in a schematic, perspective illustration, an exemplary embodiment of a protective device and a tool of a hand-held surgical device according to the invention.

FIG. 1 shows, in a schematic perspective view, an exemplary embodiment of a protective device 1, and a tool 2 of a hand-held surgical device according to the invention. For purposes of simplicity, the hand-held device, i.e. the angle piece or the handpiece, to which the protective device 1 and the tool 2 are secured, is not shown in FIG. 1 and the subsequent Figures.

It can be seen in FIG. 1 that the tool 2 is designed as a hollow cylinder, wherein a functional area 5 for machining bone is disposed on the distal edge 3 of the head 4. In the exemplary embodiment depicted here, the distal edge 4 is flat, and has a rough surface, specifically a so-called diamond coating. The protective device 1 partially encompasses the distal edge 3 of the tool 2, and extends in part over the distal edge 3. As a result, only a circular arc 6 is exposed by the protective device 1, such that this arc serves as the functional region 5 for treating the bone. Moreover, it can be derived from FIG. 1 that the protective device 1 and the tool 2, or the head 4 of the tool 2 are cylindrical. Furthermore, the protective device 1 can have adjacent, oval openings disposed on the circumference. These are not shown in FIG. 1 and the following figures, for purposes of simplicity.

Figure 2:
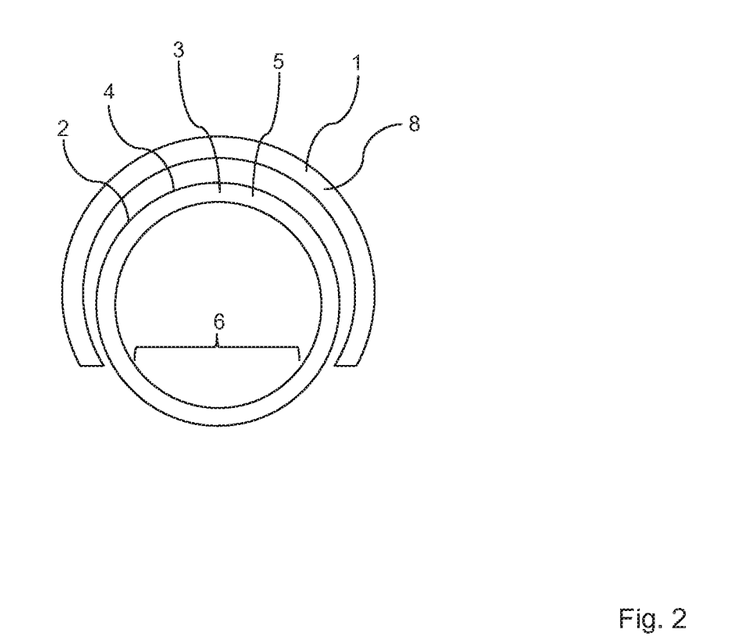
FIG. 2 shows the exemplary embodiment according to FIG. 1 in a schematic, front view.

FIG. 2 shows the exemplary embodiment according to FIG. 1 in a schematic front view. It can be clearly seen therein that the protective device 1 encompasses the head 4 of the tool 2, such that only a circular arc 6 of the distal edge 3 serves as a functional region 5. The surgeon can peel a basically half-moon shaped bone fragment out of the bone with this circular arc 6.

Figure 3:
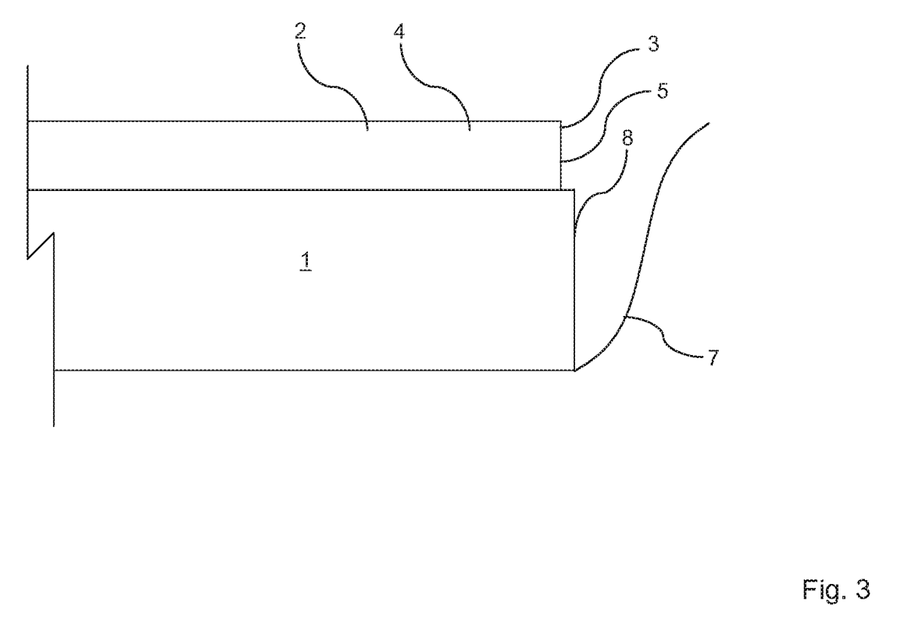
FIG. 3 shows, in a schematic, cutaway illustration, another exemplary embodiment of a protective device and a tool of a hand-held surgical instrument.

FIG. 3 shows, in a schematic, cutaway illustration, another exemplary embodiment of a protective device 1, and a tool 2 of a hand-held surgical device according to the invention. The exemplary embodiment according to FIG. 3 corresponds to the exemplary embodiment according to FIGS. 1 and 2, wherein a guide element 7, extending axially, has been added thereto. The guide element 7 serves to facilitate the insertion into the pocket between the soft tissue and bone. The guide element 7 can be made thereby from the same material as the protective device 1, and in particular, can be formed as an integral component of the protective device 1.

Figure 4:
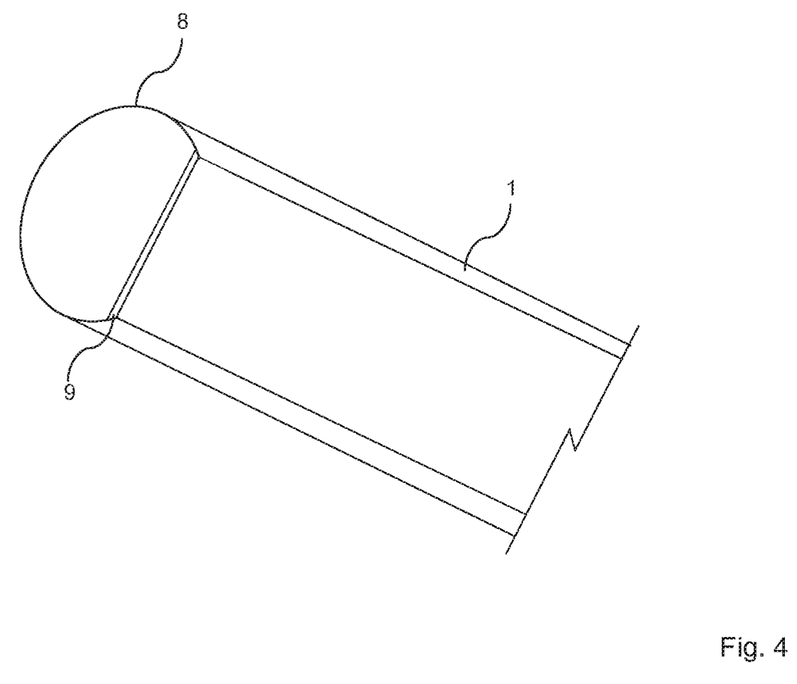
FIG. 4 shows, in a perspective view, another exemplary embodiment of a protective device according to the invention.

FIG. 4 shows, in a schematic, perspective view, another exemplary embodiment of a protective device according to the invention. For purposes of simplicity, the rotating tool 2 is not shown in FIG. 4, or FIGS. 5 and 6. In differing from the protective device 1 shown in FIGS. 1 to 3, a radial web 9 is formed on the free end 8 of the protective device, extending radially over the free end 8. The web 9 serves to prevent a penetration of the tool 2 too deep into the bone.

Figure 5:
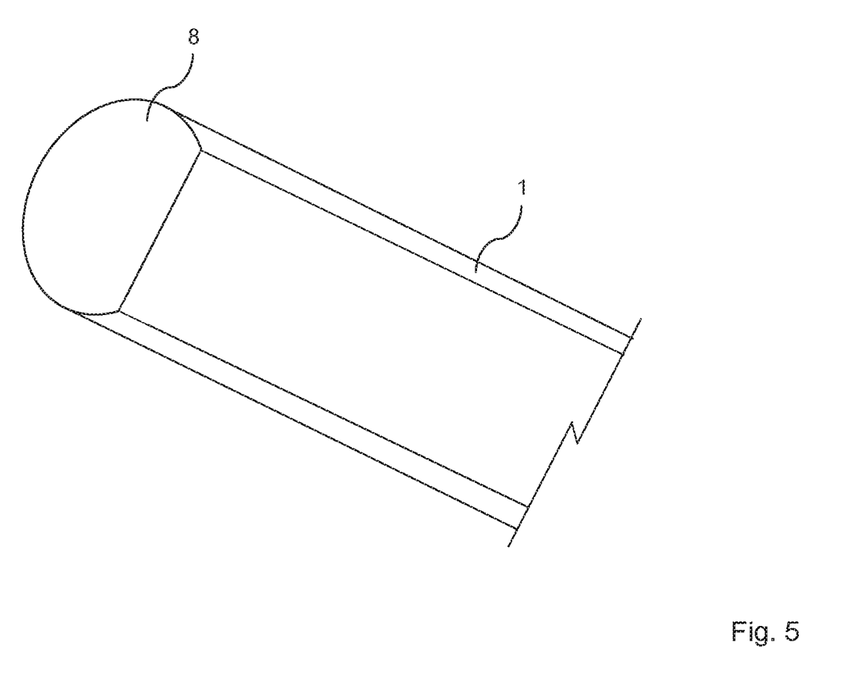
FIG. 5 shows, in a schematic, perspective view, another exemplary embodiment of a protective device according to the invention.

FIG. 5 shows, in a schematic perspective view, another exemplary embodiment of a protective device 1 according to the invention. The protective device 1 corresponds to the protective device 1 according to FIG. 4, wherein instead of a web 9, the free end of the protective device 1 is completely closed.

Figure 6:
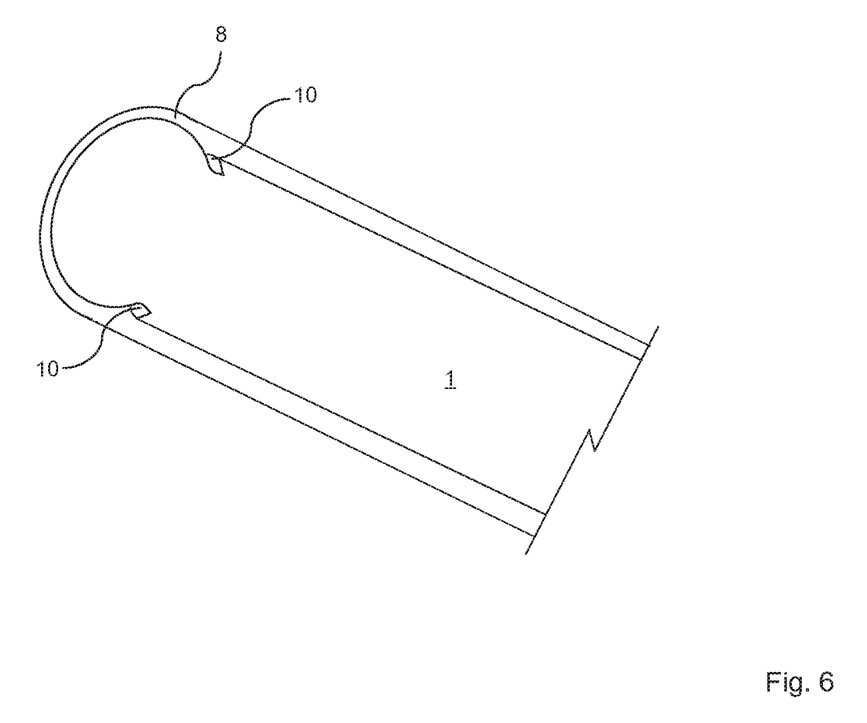
FIG. 6 shows, in a schematic, perspective view, another exemplary embodiment of a protective device according to the invention.

FIG. 6 shows, in a schematic, perspective view, another exemplary embodiment of a protective device 1 according to the invention. A radially inward extending projection 10 is formed on the free end 8 of the protective device 1. The projection 10 has the form of a collar in this exemplary embodiment, extending not only radially inward, but also axially toward the tool 2, such that the distal edge 3 of the head 4 is enclosed by the projection 10. The head 4 of the tool 2 is enclosed both radially as well as axially, or in the circumferential direction, by means of this measure, and the surrounding soft tissue is protected from injury. It is expressly noted thereby, that the projection 10 can also be designed such that it only extends radially inward, and thus covers the distal edge 3 of the tool 2 in the axial direction.

Figure 7:
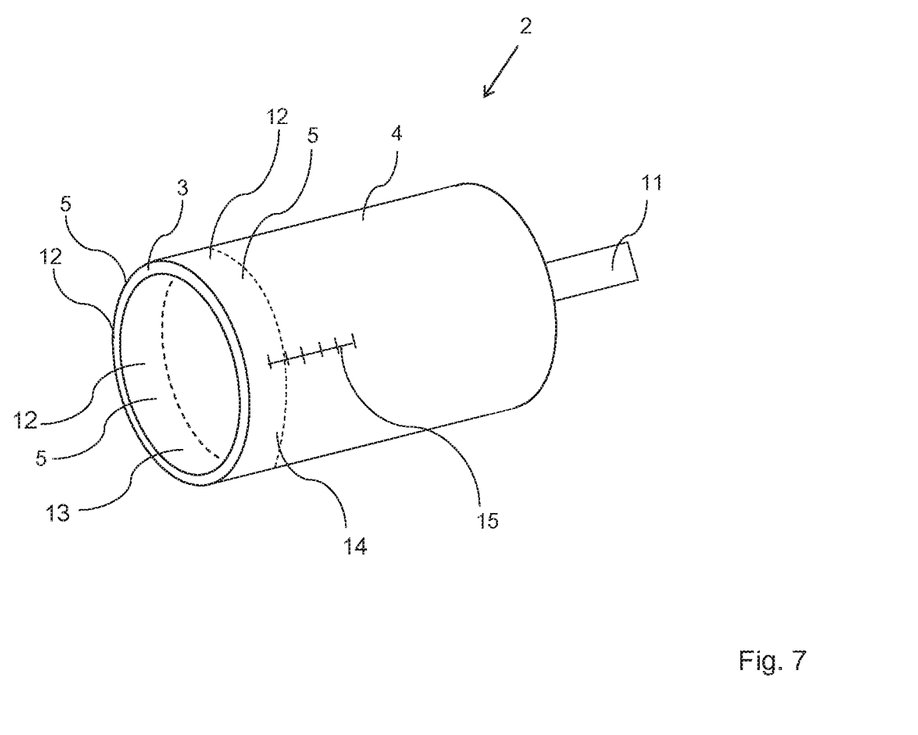
FIG. 7 shows, in a schematic, perspective view, an exemplary embodiment of the tool of a device according to the invention.

FIG. 7 shows, in a schematic, perspective view, an exemplary embodiment of the tool 2 of a device according to the invention. The tool 2 comprises a connecting region 11 for connection with a hand-held device, not shown. The hand-held device can be a conventional angle piece or handpiece, which rotates the tool 2.

The tool 2 furthermore has a hollow cylindrical head 4. A rough surface 12 is formed on the distal edge 3 of the head 2, which forms a part of the functional region 5. In the exemplary embodiment shown here, a rough surface 12—e.g. a coating with diamond grit or sapphire grit—is formed on the inner wall 13 and the outer wall 14. The extension of the rough surface 12 on the inner wall 13 and the outer wall 14 is depicted in each case by a broken line. It is, however, conceivable that the entire inner wall 13 and/or outer wall 14 is formed with a rough surface 12.

The functional region 5 as a whole is formed by the rough surface 12 on the distal edge 3, the inner wall 13, and the outer wall 14.

Moreover, markings 15 indicating a penetration depth of the head 4 into the bone are formed on the outer wall 14.

In the exemplary embodiment according to FIG. 7, the distal edge 3 is flat, i.e. it has a flat, or straight, cross section.

Figure 8:
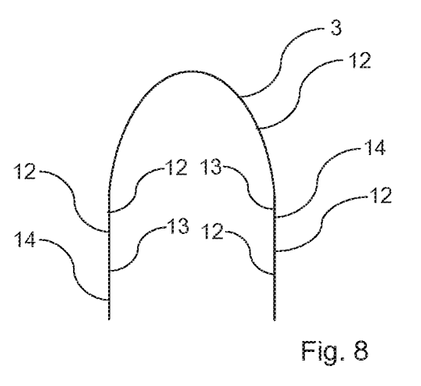
FIG. 8 shows, in a schematic depiction of another exemplary embodiment, the cross section of the distal edge of a tool of a device according to the invention.

FIG. 8 shows, in a schematic illustration of another exemplary embodiment, the cross section of the distal edge 3 of a tool 2 of a device according to the invention. The distal edge 3 has, according to FIG. 8, a convex, specifically oval, cross section. This construction is distinguished by a particularly easy penetration of the distal edge 3 into the bone. Moreover, in FIG. 8, both the inner wall 13 and the outer wall 14, as well as the distal edge 3, are provided with a rough surface 12. However, it may also be provided that just the distal edge 3, or the distal edge 3 and the inner wall 13, or the distal edge 3 and the outer wall 14, are formed with a rough surface 12.

Figure 9:
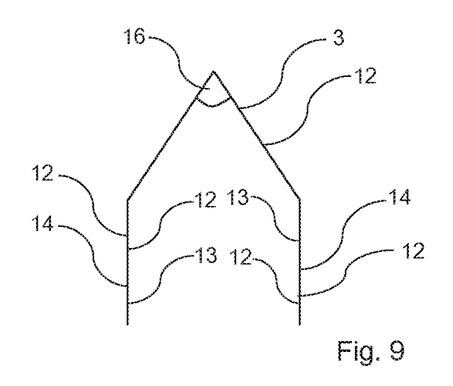
FIG. 9 shows, in a schematic depiction of another exemplary embodiment, the cross section of the distal edge of a tool of a device according to the invention.

FIG. 9 shows, in a schematic illustration of another exemplary embodiment, the cross section of the distal edge 3 of a tool 2 of a device according to the invention. In contrast to the exemplary embodiments depicted in FIG. 7 and FIG. 8, the cross section of the distal edge 3 in FIG. 9 is angular, specifically having an angle 16. It is noted at this point that the transition between the distal edge 3 and the inner wall 13, or the outer wall 14, can be angular, as depicted in FIG. 9. Moreover, this transition can be rounded. Furthermore, both the inner wall 13 and the outer wall 14, as well as the distal edge 3, are provided with a rough surface 12. However, it may also be provided that just the distal edge 3, or the distal edge 3 and the inner wall 13, or the distal edge 3 and the outer wall 14, are formed with a rough surface 12.

Figure 10:
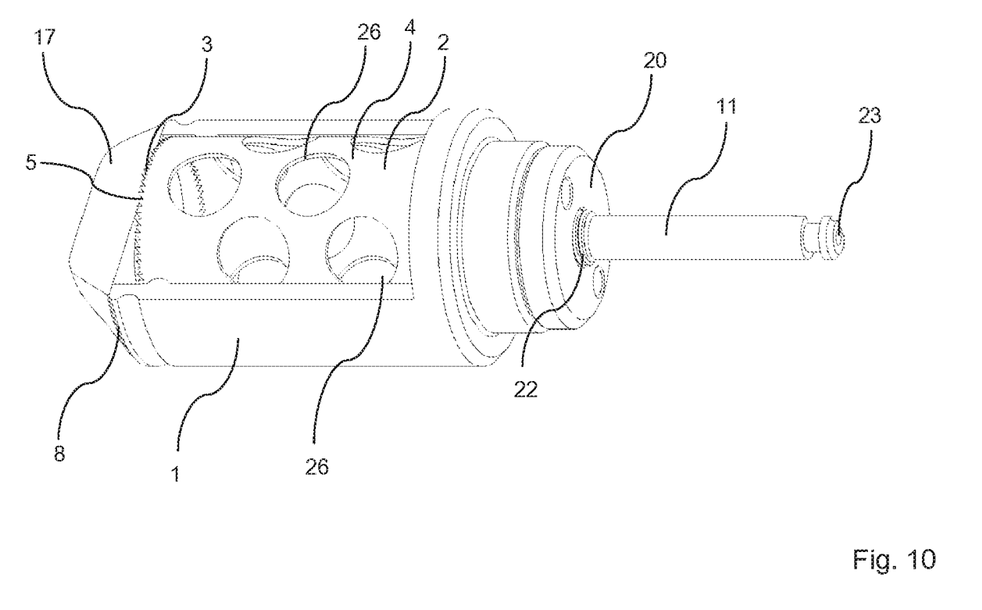
FIG. 10 shows, in a schematic depiction of another exemplary embodiment, a protective device according to the invention, with a tool.
Figure 11:
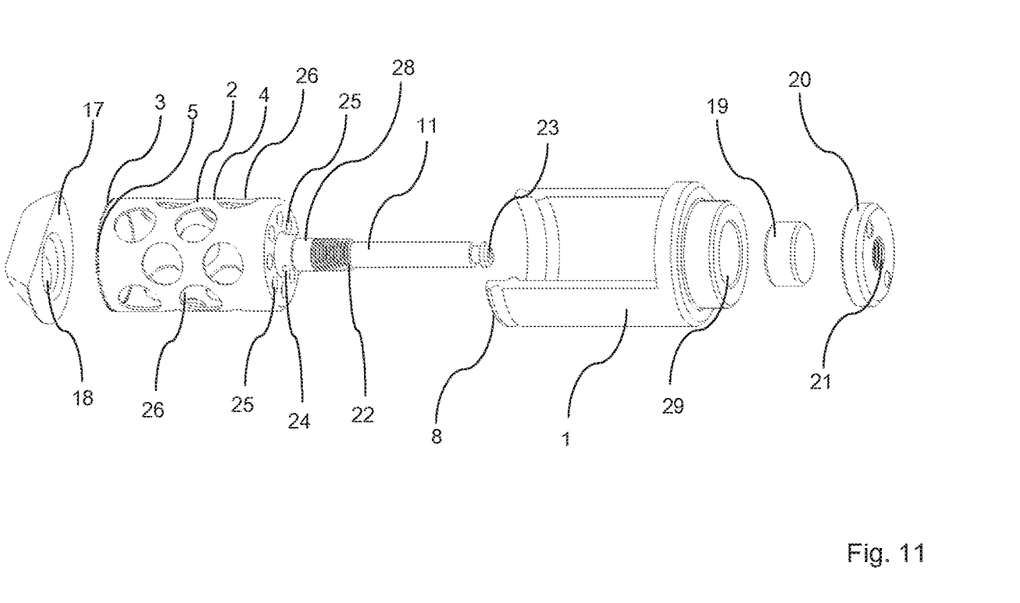
FIG. 11 shows the exemplary embodiment from FIG. 10 in a schematic exploded view.
Figure 12:
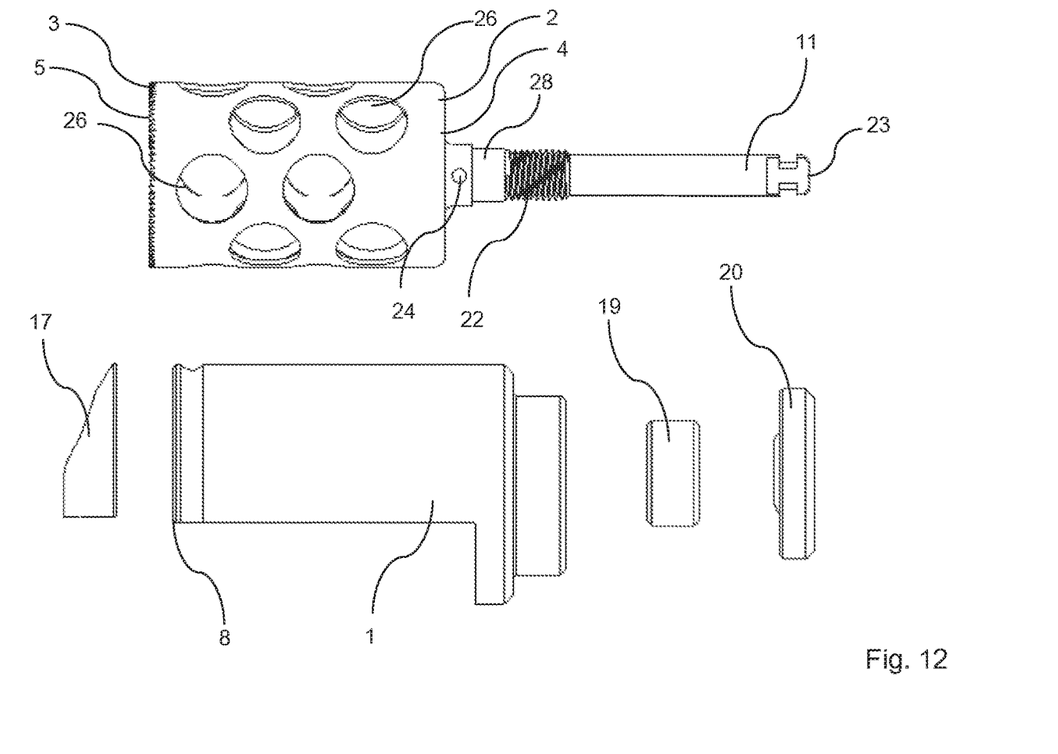
FIG. 12 shows the exemplary embodiment from FIG. 10 in another schematic exploded view.

FIGS. 10 to 12 show another exemplary embodiment of a protective device 1 according to the invention for a tool 2. In the exemplary embodiment shown here, the distal edge 3 of the head 4 has teeth, in particular saw teeth, or cutting teeth, which serve as the functional region for machining bones. Other designs of the distal edge 3 are also conceivable thereby, e.g. corresponding to FIGS. 7 to 9. Furthermore, the exemplary embodiments depicted in FIGS. 1 to 9 can comprise a tool 2, which has corresponding teeth, in particular saw teeth or cutting teeth.

The protective device 1 is substantially cylindrical, or partially cylindrical, and has a displacement element 17 on the free end 8. The displacement element 17 serves to push away the periosteum during the operation, such that the tool 2 can penetrate the bone as easily as possible. In particular, it can be clearly derived from FIG. 12 that the thickness of the displacement element 17 from the outside to the middle initially decreases, and then remains constant, by means of which the periosteum can be displaced extremely effectively.

Another advantage of the displacement element 17 is that this shields the distal edge 3 of the tool 2, such that the surrounding tissue is protected against injury. At this point, it is expressly noted that the displacement element 17 does not necessarily have to be disposed such that the protective device 1 as such encompasses the head 4 such that, specifically, only a circular arc 6 serves as the functional region 5 in the manner according to the invention. An opening 18 can be formed on the displacement element 17, through which an obtained bone piece can be removed from the interior of the device extremely easily.

The bearing 19, e.g. a ball bearing race, is also shown in FIGS. 10 to 12, via which the protective device 1 is connected to the tool 2, in particular the bearing seat 28 of the connecting region 11, or the shaft, respectively. Furthermore, a bearing receiver 29 can be formed in the protective device 1. In order to ensure a secure connection of the protective device 1 to the tool 2, in particular in the axial direction, a retention means 20—e.g. a nut—is disposed such that by means of an inner thread 21, it can be screwed onto an outer thread 22 of the connecting region 11.

As a result, the tool 2 can rotate in relation to the protective device 1, such that the protective device 1 is substantially non-rotatable during the operation, and protects the surrounding tissue in an ideal manner from injury. The connection of the protective device 1 to the hand-held surgical device, not shown, thus takes place via the shaft, or connecting region 11 of the tool 2, which serves as a connecting element. Moreover, it is conceivable that the protective device 1 is alternatively or additionally connected to the hand-held surgical device via a further—not shown connecting element. Such a further connecting element has the additional effect that the protective device 1 is non-rotatably disposed on the hand-held surgical device, such that a "coordinate rotating" with the tool 2 is avoided.

An intake 23 for a cooling liquid is formed on the proximal end of the connecting region 12, which has a flow connection to the outlet 24. The cooling liquid can be conveyed from the hand-held device, via the intake 23, to the outlet 24, wherein the cooling liquid can be introduced into the interior of the protective device 1 via the first cooling opening 25 of the tool 2. Furthermore, two cooling openings 26 are formed in the tool 2, through which the surface of the tool 2, and thus the friction with the operation point, is minimized. As a result of this measure, an overheating of the tissue or bone that is to be operated on is prevented. At this point it is noted that, for greater clarity, only some of the first cooling openings 25 and the second cooling openings 26 are provided with a reference symbol.

As can be derived from FIG. 12, the distal end of the protective device 1, specifically the displacement element 17, is formed as a separate component. The displacement element 17 can be connected to the free end 8 of the protective device 1 by means of an adhesive, for example. Advantageously, the adhesive can be selected or adjusted such that it melts when the protective device 1 is recycled, or sterilized, in particular autoclaved, such that the protective device 1 can no longer be used. Alternatively and/or additionally, the protective device can be composed at least in part of a material that changes shape and/or color when recycled.

Figure 13:
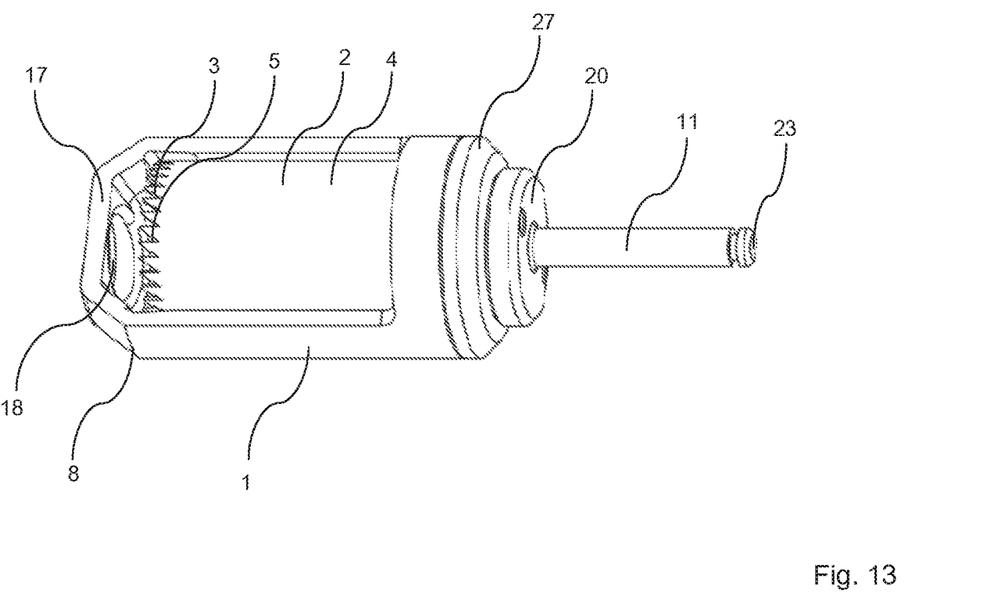
FIG. 13 shows, in a schematic depiction, another exemplary embodiment of a protective device according to the invention, with a tool.
Figure 14:
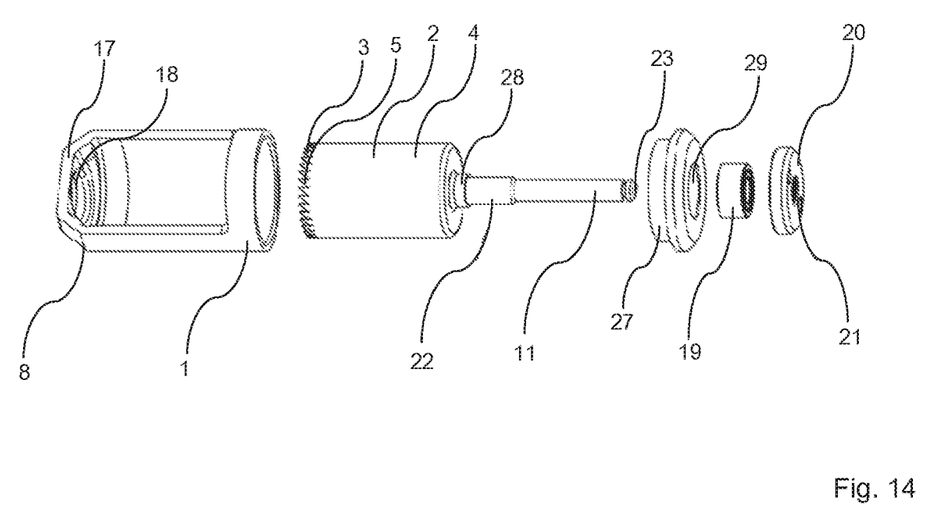
FIG. 14 shows the exemplary embodiment from FIG. 13 in a schematic exploded view.

A further exemplary embodiment of a protective device 1 according to the invention is shown with a tool 2 in FIGS. 13 and 14. The displacement element 17 is an integral component of the protective device 1 thereby, i.e. it is formed as a single piece therewith. Moreover, the proximal end 27 of the protective device 1 is designed as a separate component, and connected to the protective device 1 via an adhesive, for example. Advantageously, the adhesive can be selected or adjusted such that it melts when the protective device 1 is recycled or sterilized, in particular autoclaved, such that the protective device 1 can no longer be used.

The exemplary embodiment according to FIGS. 13 and 14 furthermore corresponds to the exemplary embodiment depicted in FIGS. 10 to 12. In particular, the tool 2 depicted in FIGS. 13 and 14 can have first cooling openings and second cooling openings, as is depicted in FIGS. 10 to 12. In order to avoid repetition, reference is made at this point to the preceding descriptions of FIGS. 10 to 12, which apply analogously to the exemplary embodiment of FIGS. 13 and 14.

Regarding further advantageous designs of the device according to the invention, in order to avoid repetition, reference is made to the general part of the description, and to the attached Claims. Lastly, it is expressly noted that the exemplary embodiments described above of the device according to the invention serve only to explain the claimed teachings, which are not, however, limited to the exemplary embodiments.

LIST OF REFERENCE SYMBOLS

1 protective device
3 distal edge
4 head
5 functional region
6 circular arc
7 guide element
8 free end
9 web
10 projection
11 connecting region
12 rough surface
13 inner wall
14 outer wall
15 markings
16 angle
17 displacement element
18 opening
19 bearing
20 retention means
21 inner thread
22 outer thread
23 intake
24 outlet
25 first cooling opening
26 second cooling opening
27 proximal end
28 bearing seat
29 bearing receiver

The invention claimed is:

1. A combination of a rotating tool and a protective device having a connecting element for releasable attachment to a hand-held surgical device, wherein a head of the rotating tool is a hollow cylinder having a rough surface or teeth disposed on a circular distal edge of the hollow cylinder and an open cavity within the hollow cylinder that receives bone cut by the rough surface or teeth, wherein the protective device is carried by the rotating tool and partially encompasses the circular distal edge of the head of the rotating tool, and wherein the protective device extends axially in part over the circular distal edge of the rotating tool such that only a circular arc of the distal edge serves as a functional cutting region of the rotating tool that cuts a partially circular bone segment usable for bone regeneration.

2. The combination according to claim 1, wherein the protective device is rotatably coupled to the tool.

3. The combination according to claim 1 or 2, wherein the protective device is coupled to the tool via a roller bearing, or a ball bearing race, or a grooved ball bearing race.

4. The combination according to claim 1, further comprising a projection extending radially inwards at a free end of the protective device.

5. The combination according to claim 1, further comprising a round web formed at a free end of the protective device.

6. The combination according to claim 5, wherein the round web extends radially over the free end.

7. The combination according to claim 1 or 2, further comprising at least one discharge opening in fluid communication with a channel extending within the protective device to supply a cooling medium to the rotating tool.

8. The combination according to claim 1 or 2, further comprising a guide element formed on the protective device.

9. The combination according to claim 4, further comprising a displacement element at the free end of the protective device projecting axially away from the free end of the protective device, wherein the displacement element has a tapered, decreasing thickness between a middle portion of the displacement element and an outer edge of the displacement element.

10. The combination according to claim 1 or 2, wherein the circular distal edge of the hollow cylinder lies in a plane transverse to a longitudinal axis of the hollow cylinder.

* * * * *